United States Patent [19]

Telschow et al.

[11] Patent Number: 5,235,085

[45] Date of Patent: Aug. 10, 1993

[54] PROCESS FOR FORMING BIS(PENTAERYTHRITOL PHOSPHATE) CARBONATE

[75] Inventors: Jeffrey E. Telschow, Tarrytown; Edward D. Weil, Hastings-on-Hudson, both of N.Y.

[73] Assignee: Akzo N.V., Arnhem, Netherlands

[21] Appl. No.: 911,826

[22] Filed: Jul. 10, 1992

[51] Int. Cl.$^5$ ................................ C07F 9/15
[52] U.S. Cl. ................................ 558/74
[58] Field of Search ............ 558/74, 277, 260, 87

[56] References Cited

U.S. PATENT DOCUMENTS

| | | | |
|---|---|---|---|
| 3,293,327 | 12/1966 | Heckenbleikner et al. | 260/936 |
| 3,873,496 | 3/1975 | Hills | 260/45.8 R |
| 4,341,694 | 7/1982 | Halpern | 252/606 |
| 4,559,180 | 12/1985 | Green | 558/277 |
| 4,652,667 | 3/1987 | Green | 558/277 |
| 4,681,967 | 7/1987 | Green | 558/277 |
| 4,801,625 | 1/1989 | Parr et al. | 558/74 |

FOREIGN PATENT DOCUMENTS 889338 2/1962 United Kingdom .

OTHER PUBLICATIONS

Boellert et al., Chem. Abst., vol. 70, #77610b (1969).

*Primary Examiner*—James H. Reamer
*Attorney, Agent, or Firm*—Richard P. Fennelly; Louis A. Morris

[57] ABSTRACT

Bis(pentaerythritol phosphate) carbonate can be formed by the reaction of pentaerythritol phosphate alcohol and dihydrocarbyl carbonate, such as diphenyl carbonate, preferably in the presence of a transesterification catalyst, such as an imidazole, and in a high boiling organic solvent, e.g., a phosphate ester solvent, which allows for removal of by-product.

20 Claims, No Drawings

PROCESS FOR FORMING BIS(PENTAERYTHRITOL PHOSPHATE) CARBONATE

BACKGROUND OF THE INVENTION

U.S. Pat. No. 4,801,625 of W. J. Parr et al. describes the carbonate derivative of pentaerythritol phosphate as a good intumescent flame retardant for such polymers as polypropylene. It also describes that it can be manufactured by reacting pentaerythritol phosphate with carbonyldiimidazole. Since carbonyldiimidazole is quite expensive, its use makes the synthesis of the carbonate derivative rather expensive. A need exists for a less expensive synthetic procedure for the manufacture of the pentaerythritol phosphate carbonate flame retardant additive.

SUMMARY OF THE PRESENT INVENTION

The present invention relates to a process for forming bis(pentaerythritol phosphate) carbonate by the reaction of pentaerythritol phosphate alcohol and a dihydrocarbyl (e.g., dialkyl or diaryl) carbonate, preferably by reaction in an organic solvent, such as an aryl phosphate solvent, using a catalyst such as an imidazole catalyst.

DETAILED DESCRIPTION OF THE INVENTION

The pentaerythritol phosphate alcohol reagent which is employed in the present process is described in a number of prior art patents including the aforementioned U.S. Pat. No. 4,801,625 as well as U.S. Pat. Nos. 3,873,496 and 4,341,694 and British Patent No. 889,338.

The other essential reagent for use in the present process is dihydrocarbyl carbonate, such as diphenyl carbonate which has the formula $(C_6H_5O)_2C=O$, dimethyl carbonate which has the formula $(CH_3O)_2C=O$ or diethyl carbonate which has the formula $(CH_3CH_2O)C=O$. The hydrocarbyl group in the carbonate reagent can be selected from such known hydrocarbyl groups as the alkyl and aryl groups known to the person of ordinary skill in the art. It is necessary that the resulting carbonate reagent have a boiling point which is sufficiently high to insure that it is in the reaction medium, under the pressure conditions used, for reaction with the previously described alcohol reagent.

The reaction of the foregoing types of reagents needs to be carried out at temperatures sufficiently elevated to insure reaction between the alcohol reagent, which has a hindered orientation for the alcohol reaction site, and the selected carbonate. It is deemed that temperatures of from about 150° C. to about 250° C. can be used, with molar ratios of the respective reagents ranging from about 1.5:1 to about 3:1. The reaction is preferably conducted in a suitable high boiling organic solvent, such as an organic phosphate ester, which allows for the removal of alcohol by-product, for example, phenol by-product when diphenyl carbonate is one of the reagents, from the reaction medium, preferably at reduced pressure in substantially pure form without contamination due to solvent co-distillation. The organic phosphate ester contemplated for use in a preferred embodiment of the invention is a neutral ester of a phosphorus acid in the +5 oxidation state which is stable (free of acid generation) at the selected reaction temperature. A preferred solvent for use is a liquid aryl phosphate ester such as triphenyl phosphate, cresyl diphenyl phosphate, tricresyl phosphate, isopropylphenyl diphenyl phosphate, t-burylphenyl diphenyl phosphate, and tetraphenyl resorcinol diphosphate.

In order to achieve the highest yield of product, it is also preferred to utilize a transesterification catalyst for the reaction, for example, a high boiling amine such as tribenzylamine, diazabicyclooctane, or N,N,N,-tetramethyl-butanediamine, an alkali metal (e.g., sodium) salt of a phenol, or, preferably, an imidazole catalyst which is best at giving a low-color or uncolored product in high yield. The imidazole catalyst can be imidazole or an alkyl-substituted imidazole.

The crude product from the reaction described hereinbefore precipitates from the reaction medium during the synthesis and can be filtered, washed with solvent (e.g., methanol), and dried. The melting point of the product is over 300° C. and representative yields of crude product are in the range of from about 80% to about 95%. The mother liquors and catalyst from the reaction can be recycled. The reaction product can be purified by stirring a suspension of it in warm dimethylsulfoxide, filtering the undissolved solid, and precipitating purified product by addition of a nonsolvent, such as methanol.

The following Examples illustrate certain embodiments of the present process.

EXAMPLE 1

A three liter, four-necked flask was fitted with a mechanical stirrer, pot thermometer, and 5½ inch Vigreux column topped with a distilling head. Into this were placed 450 g (2.50 moles) of pentaerythritol phosphate alcohol (PEPA or 2,6,7-trioxa-1-phosphabicyclo[2.2.2]octane-4-methanol-1-oxide), 286 g (1.34 moles) of diphenyl carbonate, 8.5 g (0.125 mole) of imidazole, and 1250 mL of an isopropylated triphenyl phosphate (i.e., PHOSFLEX 41P brand) under nitrogen. The mixture was evacuated to 70 mm Hg pressure, stirred well, and heated to 204° C. over thirty-five minutes. Rapid distillation of phenol began, and the reaction mixture was heated at 200°–205° C. for two hours, followed by another two hours at 210°–215° C. At this point, the phenol had ceased distilling (recovered 213.0 g, 90.6% yield and 99.2% pure by GC analysis), and the reaction was cooled to 50° C., returned to atmospheric pressure with nitrogen, and filtered. The solid was washed three times with 400 mL portions of methanol and was then dried for five hours at 120° C./4 mm Hg to give 420.3 g (87.0% yield) of pale cream-colored bis-PEPA carbonate (BPC). The solid decomposed without melting at over 300° C. and showed a singlet at −6.4 ppm by $^{31}P$ NMR ($d_6$-DMSO).

EXAMPLE 2

The mother liquors from Example 1 were stripped under vacuum to remove methanol, returned to the same three liter reactor along with an additional 75 mL of isopropylated triphenyl phosphate (PHOSFLEX 41P brand) and recharged with another 450 g of PEPA and 286 g of diphenyl carbonate. No additional imidazole was added. The reaction was repeated as above to give 465.1 g (96.3% yield) of yellowish BPC and 202.0 g (86.0%) of 99.2% pure phenol.

EXAMPLES 3–8

For the following Examples, a 250 ml four-necked reactor was fitted as in Example 1 and was charged with 45 g (0.25 mole) of PEPA, 26.8 g (0.125 mole) of diphenyl carbonate, and 125 mL of the PHOSFLEX 41P brand material. The amount of catalyst shown in Table 1 was added, followed by the same heating, distillation and filtration procedures as described in Example 1.

TABLE 1

| Catalyst | Amount (g) | Temp (°C.) | Time (hr) | Yield BPC (g/%) | Notes |
| --- | --- | --- | --- | --- | --- |
| Imidazole | 1.7 | 200 | 5 | 42.7/88.4 | light pink solid; phenol was not distilled |
| Na/Phenol | 0.29/1.18 | 202 | 3 | 37.7/78.1 | White solid |
| Na/Phenol/Imidazole | 0.23/0.94/0.17 | 200 | 3 | 34.1/74.1 | light pink solid |
| Tribenzylamine | 3.5 | 220 | 2 | 17.0/35.2 | Tan solid; dark brown solution |
| Tetraisopropyl titanate | 3.5 | 200 | 2 | 2.0/4.4 | Tan solid; black crust forms on reactor walls |
| Methanesulfonic acid | 1.2 | 200 | 3 | 0.0 | Reaction mixture turned black |

We claim:

1. A process for forming bis(pentaerythritol phosphate) carbonate which comprises the reaction of pentaerythritol phosphate alcohol and dihydrocarbyl carbonate.

2. A process as claimed in claim 1 wherein the reaction is carried out in the presence of a transesterification catalyst.

3. A process as claimed in claim 2 wherein the catalyst is an imidazole compound.

4. A process as claimed in claim 1 wherein the reaction is performed in an aryl phosphate ester solvent.

5. A process as claimed in claim 4 wherein the reaction is carried out in the solvent in the presence of a transesterification catalyst.

6. A process as claimed in claim 5 wherein the catalyst is an imidazole compound.

7. A process as claimed in claim 1 wherein the molar ratio of pentaerythritol phosphate to dihydrocarbyl carbonate is from about 1.5:1 to about 3:1.

8. A process as claimed in claim 7 wherein the reaction is carried out in the presence of a transesterification catalyst selected from the group consisting of an alkali metal salt of a phenol and an imidazole compound and in an aryl phosphate ester solvent.

9. A process as claimed in claim 8 wherein the catalyst is an imidazole compound.

10. A process as claimed in claim 7 wherein the temperature of reaction is from about 150° C. to about 250° C.

11. A process for forming bis(pentaerythritol phosphate) carbonate which comprises the reaction of pentaerythritol phosphate alcohol and diphenyl carbonate.

12. A process as claimed in claim 11 wherein the reaction is carried out in the presence o a transesterification catalyst.

13. A process as claimed in claim 12 wherein the catalyst is an imidazole compound.

14. A process as claimed in claim 11 wherein the reaction is performed in an aryl phosphate ester solvent.

15. A process as claimed in claim 14 wherein the reaction is carried out in solvent in the presence of a transesterification catalyst selected from the group consisting of an alkali metal salt of a phenol and an imidazole compound.

16. A process as claimed in claim 15 wherein the catalyst is an imidazole compound.

17. A process as claimed in claim 11 wherein the molar ratio of pentaerythritol phosphate to diphenyl carbonate is from about 1.5:1 to about 3:1.

18. A process as claimed in claim 17 wherein the reaction is carried out in the presence of a transesterification catalyst and in an aryl phosphate ester solvent.

19. A process as claimed in claim 18 wherein the catalyst is an imidazole compound.

20. A process as claimed in claim 17 wherein the temperature of reaction is from about 150° C. to about 250° C.

* * * * *

UNITED STATES PATENT AND TRADEMARK OFFICE
CERTIFICATE OF CORRECTION

PATENT NO. : 5,235,085
DATED : August 10, 1993
INVENTOR(S) : Jeffrey E. Telschow and Edward D. Weil It is certified that error appears in the above-identified patent and that said Letters Patent is hereby corrected as shown below:

Col. 2, line 2, "t-burylphenyl" should read -- t-butylphenyl --;
Col. 2, line 3, "dihosphate" should read -- diphosphate --;
Col. 4, Claim 12, line 2, "o" should read -- of --.

Signed and Sealed this

Fifteenth Day of March, 1994

BRUCE LEHMAN

*Attest:*

*Attesting Officer*    Commissioner of Patents and Trademarks